United States Patent [19]
Oglevee-O'Donovan et al.

[11] Patent Number: 5,514,580
[45] Date of Patent: May 7, 1996

[54] IN VITRO LEAF PETIOLE MULTIPLICATION OF PELARGONIUMS

[75] Inventors: Wendy Oglevee-O'Donovan, Scottdale; Eleanor Stoots, Connellsville, both of Pa.

[73] Assignee: Oglevee, Ltd., Connellsville, Pa.

[21] Appl. No.: 149,702

[22] Filed: Nov. 9, 1993

Related U.S. Application Data

[63] Continuation of Ser. No. 690,073, Apr. 23, 1991, abandoned.

[51] Int. Cl.$^6$ ................................ C12N 5/00; C12N 5/02
[52] U.S. Cl. ................................ 435/240.45; 435/240.1; 435/240.4; 435/240.54; 47/DIG. 3; 47/DIG. 6; 800/DIG. 22
[58] Field of Search ........................... 435/240.4, 240.45, 435/240.48, 240.1, 240.54; 800/DIG. 22; 47/DIG. 3, DIG. 6

[56] References Cited

U.S. PATENT DOCUMENTS

| | | | |
|---|---|---|---|
| 4,897,957 | 2/1990 | Oglevee et al. | 800/DIG. 22 |
| 4,931,394 | 6/1990 | Krul | 435/240.45 |

OTHER PUBLICATIONS

[1]Marsolais et al., "Somatic embryogenesis and artificial seed production in Zonal (Pelargonium x hortorum) and Regal (Pelargonium x domesticum) geranium," Can. J. Bot., vol. 69, pp. 1188–1193 (1991).
The Sigma Catalogue—Biochemicals, Organic Compounds for Research & Diagnostic Reagents, pp. 1415–1421 (1991).
Edwin G. George et al., Plant Propagation by Tissue Culture; Handbook and Directory of Commercial Laboratories, Chapter 9, Progress in Micropropagation, 1984, pp. 389–411.

Philip V. Ammirato et al., Handbook of Plant Cell Culture, vol. 5, Ornamental Species, Chapter 19 "Geranium (Pelargonium)", 1990, pp. 439–460.
Skirvin et al, J. Amer. Soc. Hort. Sci., 101(3) pp. 281–290 (1976).
Cassells et al, Acta Horticulturae, 212, pp. 419–423 (1987).
White et al, J. Amer. Soc. Hort. Sci., 113(3), pp. 354–359 (1988).
Erickson et al, HortScience, 15(6), pp. 815–817, (1980).
Vetanovetz et al, HortScience, 20(4), pp. 703–705 (1985).
Conger, Cloning Agricultural Plants Via In Vitro Techniques, chapter 2, pp. 5–50 (1986).
1. A. B. Grat, Exotica—Pictorial Cyclopedia of Exotic Plants, Ed. 7, p. 882.

*Primary Examiner*—Michael G. Wityshyn
*Assistant Examiner*—Susan M. Dadio
*Attorney, Agent, or Firm*—Webb Ziesenheim Bruening Logsdon Orkin & Hanson

[57] ABSTRACT

A process for propagating *Pelargonium x domesticum* varieties by tissue culture propagation of petiole sections taken from a mother plant. In addition to tissue culture propagation steps and growth media constituents which are known in the art, an essential step of the preferred embodiment of the invention includes the conducting of callus formation by initial culturing of the petiole section in the dark. In all embodiments of the invention, however, it is believed that the effectiveness of the present process is attributable at least in part to the presence in the culture medium of a growth regulator selected from the group consisting of amino or benzyl-glucosides and amino- or benzyl-glycosides or any other composition chemically equivalent to the exemplary regulator benzylamino riboside.

7 Claims, No Drawings

IN VITRO LEAF PETIOLE MULTIPLICATION OF PELARGONIUMS

This is a continuation of application Ser. No. 07/690,073, filed on Apr. 23, 1991, now abandoned.

FIELD OF THE INVENTION

The present invention relates to tissue culture medium propagation of plants of the species *Pelargonium x domesticum*.

BACKGROUND OF THE INVENTION

Traditionally, commercial propagation of *Pelargonium x domesticum* (Regal Pelargoniums, or "Martha Washington Geraniums" as distinct from other geraniums) has been effected primarily if not exclusively by vegetative propagation of cuttings. Even though certain other plants may easily be propagated by in vitro tissue culture techniques, earlier attempts at reliable propagation of *Pelargonium x domesticum* by tissue culture have been unsatisfactory if not completely unsuccessful.

For example, as reported by Cassells, A.C., and Carney, B.F., "Adventitious regeneration in *Pelargonium x domesticum* Bailey," *Acta Horticulturae*, 212(II), 419–425 (1987), in stem and petiole tissue cultures of Grand Slam (as an example of *P. domesticum*), up to 16% of the adventitious regenerants were variants, depending on the explant origin. Controls, whether stem cuttings or in vitro nodal cultures, yielded no variants. The authors concluded that genome instability in Grand Slam and presumably other *P. domesticum* varieties may produce useful variation but mitigates against the use of adventitious regeneration in micropropagation.

These findings are consistent with the earlier work of Skirvin, R.M. and Janick, Jules, "Tissue Culture-induced Variation in Scented Pelargonium ssp.," *J. Amer. Soc. Hort. Sci.*, 101(3), 281–290 (1976). Skirvin et al. compared tissue culture propagated Pelargonium plants (from root cuttings, petiole cuttings or calliclones) with plants derived from vegetative propagation, i.e., stem cuttings. The plants derived from stem cuttings were all uniform and identical to the parental clone, whereas those from the root cuttings, petiole cuttings or calliclones were all morphologically distinct with the degree of variability depending on the cultivar. The authors conclude that the variability associated with calliclones derived from tissue culture is a pool on which selection can be imposed, implying conversely that tissue culturing of this type is inappropriate for use in attempting reliable regeneration of *Pelargonium x domesticum*.

Accordingly, a need remains for a reliable and commercially viable tissue culture propagation technique for *Pelargonium x domesticum* varieties.

SUMMARY OF THE INVENTION

In order to meet this need, the present invention is a process for propagating *Pelargonium x domesticum* varieties by culturing petiole sections taken from a mother plant. The process inhibits or eliminates morphologic variation beyond slight variations which are commercially acceptable. In addition to tissue culture propagation steps and growth media constituents which are known in the art, an essential step of the preferred embodiment of the invention includes the conducting of callus formation in the dark. In all embodiments of the invention, however, it is believed that the effectiveness of the present process is attributable at least in part to the presence in the growth medium of a growth regulator selected from the group consisting of amino- or benzyl-glucosides and amino- or benzyl-glycosides or any other composition chemically equivalent to the exemplary growth regulator benzylamino riboside. Additional optional growth regulators including oxins and kinins (indole-butyric acid, benzylamine, benzyladenine, benzylaminopurine, alpha naphthylacetic acid, and others known in the art) may also be present.

DETAILED DESCRIPTION OF THE INVENTION

The present invention is a process for the tissue culture propagation of *Pelargonium x domesticum*. As explained in greater detail below, the process inhibits or eliminates morphologic variation (beyond variations considered to be unimportant for commercial purposes) so that tissue culture propagation of all *Pelargonium x domesticum* varieties is both possible and feasible. The process is especially commercially viable due to the use of leaf petiole explants, inasmuch as leaf petioles are abundant and may be harvested from stock plants with impunity. In addition to tissue culture propagation steps and growth media constituents which are known in the art, it is believed that the effectiveness of the present process is attributable at least in part to callus formation and/or the presence in the growth medium of a growth regulator selected from the group consisting of amino- or benzyl-glucosides and amino- or benzylglycosides. Exemplary of such growth regulators is the compound benzylamino riboside. Additional optional growth regulators including oxins and kinins (indolebutyric acid, benzylamine, benzyladenine, benzylaminopurine, alpha naphthylacetic acid, and others) may also be present. In the preferred embodiment of the invention, callus formation (or at least initial callus formation) is conducted in the dark.

The process has commercial viability in that it can be used without modification in the propagation of Pelargonium species and varieties, resulting in both reliable propagation and industrial efficiency.

The process according to the preferred embodiment can be generally described as follows. Leaves are harvested from stock plants for which propagation is desired. The petiole section of each leaf is sterilized with a soap-and-water wash followed by surface sterilization with a solution containing soap and hypochlorite bleach. (Although theoretically other plant members besides the petiole should be manipulable for tissue culture propagation, surprisingly only the petioles have yielded good results to date.) Three sterile water rinses follow the soap and bleach application, and the petiole is then allowed to remain moist.

Each petiole is then cut into 1 cm. lengths (the length is not critical) and each length is placed in a separate test tube or vial containing culture medium. The culture medium contains vitamins, minerals, a food source and at least one growth regulator. The food source usually includes the Murashige Skoog salt known in the art, and may (but need not) also include additional food or energy sources such as fresh coconut milk. One growth regulator is selected from the group consisting of amino- or benzyl-glucosides and amino- or benzyl-glycosides or other growth regulators chemically equivalent to the exemplary compound benzylamino riboside. Additional oxin and/or kinin growth regulators (indole acetic acid, indole-butyric acid, benzylamine, benzyladenine, benzylaminopurine, alpha naphthylacetic acid, and others) may also be present.

The test tubes are maintained for 2 weeks in complete darkness, at a temperature of 72° F. (22.2° C.). Over the two week period, the section enlarges slightly and the ends become callused. Miniature shoots start forming intermittently on the callused ends of the petiole section.

After 2 weeks the enlarged petiole section bearing the miniature shoots is transferred from the test tube or vial to a Magenta vial or box known in the art. The enlarged petiole sections are housed five-to-a-Magenta vial. The same growing media as was originally charged to the test tube or vial is likewise charged to the Magenta vial, although if coconut milk was omitted during initial callus formation an aliquot of it should be added to the Magenta vial. The Magenta vials are then maintained, under the same conditions as were the test tubes, for an additional 4 weeks in the dark and at 72° F. The Magenta vials are then exposed to 5 weeks of 16 hours of light daily, in which the temperature is maintained at 72° F. (22.2° C.) with 690 foot candles (6900 lux) of cool fluorescent light. During this time the petiole sections grow into enlarged clumps; the shoots elongate and turn into plantlets and many more shoots form.

After a total of 11 weeks have elapsed, the clumps are removed and placed in sterile water. The individual plants are dissected out of the clump with a sterile scalpel. Each individual plant essentially has a series of leaves and nodes and is at least ½ high, but no roots are present. The individual plants are placed in RUBBER DIRT™ or other soil or soil-like growth media or growth media plugs, where rooting then takes place. Many varieties of *Pelargonium x domesticum* have been successfully tissue cultured through leaf petioles and multiplied. Variation has been minimal and within commercially acceptable limits for finished plant material.

Embodiments of the invention other than the preferred embodiment utilize petioles for in vitro tissue culture propagation, but do not include callus formation in the dark. Various embodiments other than the preferred embodiment of the invention therefore generally follow the following steps. Leaves are harvested from stock plants for which propagation is desired. The petiole section of each leaf is sterilized with a soap-and-water wash followed by surface sterilization with a solution containing soap and hypochlorite bleach. Three sterile water rinses follow the soap and bleach application, and the petiole is then allowed to remain moist.

Each petiole is then cut into 1 cm. (size not critical) lengths and each length is placed in a separate test tube or vial containing culture medium. The culture medium contains vitamins, minerals, a food source and at least two growth regulators. The food source includes the Murashige Skoog salt known in the art, and may also include additional food or energy sources such as fresh coconut milk. At least one growth regulator is selected from the group consisting of amino- or benzyl-glucosides and amino- or benzyl-glycosides. Exemplary of such growth regulators is the compound benzylamino riboside. Additional optional growth regulators including oxins and kinins (indole acetic acid, indole-butyric acid, benzylamine, benzyladenine, benzylaminopurine, alpha naphthylacetic acid, and others) may be added.

The test tubes are maintained for 8 weeks at 16 hours of light daily, temperature 72° F. (22.2° C.) with 690 foot candles (6900 lux) of cool fluorescent light. Over the eight week period, the section enlarges slightly and the ends become callused. Miniature shoots start forming intermittently on the callused ends of the petiole section.

After 8 weeks the enlarged petiole section bearing the miniature shoots is transferred from the test tube or vial to a Magenta vial or box known in the art. The enlarged petiole sections are housed four-to-a-Magenta vial. The same growing media as was originally charged to the test tube or vial is likewise charged to the Magenta vial. The Magenta vials are then maintained, under the same conditions as were the test tubes, for an additional 7 weeks. During this time the petiole sections grow into enlarged clumps; the shoots elongate and turn into plantlets and many more shoots form.

After the 7 weeks have elapsed, the clumps are removed and placed in sterile water. The individual plants are dissected out of the clump with a sterile scalpel. Each individual plant essentially has a series of leaves and nodes and is at least ½ high, but no roots are present. The individual plants are placed in RUBBER DIRT[198] or other soil or soil-like growth media or growth media plugs, where rooting then takes place.

One advantage offered by the preferred embodiment of the invention over the other embodiments of the invention is minimized time. According to the above description, the preferred embodiment of the invention requires 11 weeks of in vitro propagation prior to rooting, whereas the other embodiments of the invention require 15 weeks. Even individuals otherwise unfamiliar with commercial propagation can readily appreciate the vast technical and commercial advancement the preferred embodiment affords. Even at that, the other embodiments of the invention offer tremendous cost/time efficiency and economy over previously used methods. Before the development of the present invention, a mother plant had to grow for an entire year after meristem tissue culture before a total of 40 cuttings of the mother plant could be taken. With the present invention, however, a typical plant having 40 leaves yields 4800 new plants (40 leaves×4 pieces per petiole×30 plants per clump=4800). This high producing technique also affords reliable propagation which, for whatever reason, could not be achieved according to the methods of the prior art.

The following examples will further illustrate the method of the present invention.

EXAMPLE 1

Forty leaves were harvested from a *Pelargonium x domesticum* stock plant for which propagation was desired. The petiole section of each leaf was sterilized with a soap-and-water wash followed by surface sterilization with a solution containing soap and 25% hypochlorite bleach. Three sterile water rinses followed the soap and bleach application.

Each petiole was then cut into 1 cm. lengths and each length was placed in a separate test tube containing culture medium. The culture medium contained vitamins, minerals, a food source and two growth regulators. The food source was a two-thirds aqueous solution of Murashige Skoog salt, and benzylamino riboside (four parts per million) and indole-butyric acid (ten parts per million) were the growth regulators selected.

The test tubes were maintained for 2 weeks in complete darkness, at a temperature of 72° F. (22.2° C.). Over the two week period, the section enlarged slightly and the ends became callused. Miniature shoots started forming intermittently on the callused ends of the petiole section.

After 2 weeks the enlarged petiole section bearing the miniature shoots was transferred from the test tube to a Magenta box. The enlarged petiole sections are housed five-to-a-Magenta box. The same growing media as was originally charged to the test tube or vial was charged to the Magenta vial together with approximately 10% by volume fresh coconut milk. The Magenta boxes were then maintained, under the same conditions as the test tubes were, for an additional 4 weeks in the dark and at 72° F. The Magenta boxes were then exposed to 5 weeks of 16 hours of light daily, in which the temperature was maintained at 72° F. (22.2° C.) with 690 foot candles (6900 lux) of cool fluorescent light. During this time the petiole sections grew into enlarged clumps; the shoots elongated and transformed into plantlets and many more shoots were formed.

After a total of 11 weeks, the clumps were removed and placed in sterile water. The individual plants were dissected out of the clump with a sterile scalpel. Each individual plant included a series of leaves and nodes and was at least ½" high, but no roots were present. The individual plants were placed in RUBBER DIRT™ growth media plugs, where rooting was then permitted to take place.

EXAMPLE 2

Forty leaves were harvested from a stock plant. The petiole section of each leaf was sterilized with a soap-and-water wash followed by surface sterilization with a solution containing soap and 25% hypochlorite bleach. Three sterile water rinses followed the soap and bleach application.

Each petiole was then cut into 1 cm. lengths and each length was placed in a separate test tube containing culture medium. The culture medium contained vitamins, minerals, a food source and two growth regulators. The food source was a two-thirds aqueous solution of Murashige Skoog salt, approximately 10% by volume of coconut milk, and the growth regulators were benzylamino riboside (4 p.p.m.) and indole-butyric acid (10 p.p.m.).

The test tubes were maintained for 8 weeks at 16 hours of light daily, temperature 72° F. (22.2° C.) with 690 foot candles (6900 lux) of cool fluorescent light. Over the eight week period, the petiole sections enlarged slightly and the ends became callused. Miniature shoots started forming intermittently on the callused ends of the petiole section.

After 8 weeks the enlarged petiole section bearing the miniature shoots was transferred from the test tube or vial to a Magenta vial. The enlarged petiole sections were housed four-to-a-Magenta vial. The same growing media as was originally charged to the test tube or vial was likewise charged to the Magenta vial. The Magenta vials were then maintained, under the same conditions as were the test tubes, for an additional 7 weeks. During this time the petiole sections grew into enlarged clumps; the shoots elongated and became plantlets, and many more shoots formed.

After the total of 15 weeks elapsed, the clumps were removed and were placed in sterile water. The individual plants were dissected out of the clump with a sterile scalpel. Each individual plant essentially had a series of leaves and nodes and was at least ½" high, but no roots were present. The individual plants were placed in RUBBER DIRT™ or other soil or soil-like growth media or growth media plugs, where rooting took place.

CONCLUSION

Although the invention has been described with particularity above, the invention is only to be limited insofar as is set forth in the accompanying claims.

We claim:

1. A method for propagating a *Pelargonium x domesticum* mother plant, comprising the steps of:
    a) harvesting one or more petioles from a *Pelargonium x domesticum* mother plant;
    b) culturing solely petiole tissue from the petioles harvested in step a) in a culture medium, said culture medium containing benzylaminoriboside, in the dark;
    c) exposing said petiole tissue from step b) to periods of light and darkness;
    d) removing small plants from a clump of small plants resulting from the culturing of said petiole tissue; and
    e) rooting and growing said small plants, whereby substantially uniform plants are produced.

2. The method according to claim 1 wherein said culture medium additionally comprises nutrients.

3. The method according to claim 1 wherein said culture medium additionally comprises vitamins, minerals and a food source.

4. The method according to claim 1 wherein said culture medium additionally comprises vitamins, minerals, Murashige Skoog salt and coconut milk.

5. The method according to claim 1 wherein step b) is conducted over a period of two weeks and wherein step c) is conducted over a period of at least four weeks in the dark and then daily periods of light for at least five weeks.

6. The method according to claim 1 including placing said petiole tissue in a Magenta box prior to exposing said petiole tissue to periods of light and darkness, whereby said method eliminates morphologic variation within commercial acceptability.

7. A method for propagating a *Pelargonium x domesticum* mother plant, comprising the steps of:
    a) harvesting one or more petioles from a *Pelargonium x domesticum* mother plant;
    b) culturing solely petiole tissue from the petioles harvested in step a) in a culture medium, said culture medium containing benzylaminoriboside, in the dark;
    c) exposing said petiole tissue from step b) to periods of light and darkness;
    d) removing small plants from a clump of small plants resulting from the culturing of said petiole tissue;
    e) rooting and growing said small plants; and
    f) repeating steps a)-e) to yield at least 4800 small plants from said *Pelargonium x domesticum* mother plant whereby said small plants are substantially uniform.

* * * * *